(12) United States Patent
Slade

(10) Patent No.: US 6,631,891 B1
(45) Date of Patent: Oct. 14, 2003

(54) VOLATILE MATERIAL DISPENSERS

(76) Inventor: Brian Slade, 20 Star Road, Ashford, Kent TN24 8BX (GB)

(*) Notice: Subject to any disclaimer, the term of this patent is extended or adjusted under 35 U.S.C. 154(b) by 0 days.

(21) Appl. No.: 09/856,535

(22) PCT Filed: Nov. 25, 1999

(86) PCT No.: PCT/GB99/03938

§ 371 (c)(1),
(2), (4) Date: Jul. 20, 2001

(87) PCT Pub. No.: WO00/30692

PCT Pub. Date: Jun. 2, 2000

(30) Foreign Application Priority Data

Nov. 26, 1998 (GB) .......................... 98309727

(51) Int. Cl.[7] .................................. B01F 3/04
(52) U.S. Cl. .............................. 261/104; 261/DIG. 88; 239/44
(58) Field of Search ................ 261/104, 107, 261/DIG. 88; 239/43, 44, 45, 53

(56) References Cited

U.S. PATENT DOCUMENTS

| | | | |
|---|---|---|---|
| 1,962,100 A | * | 6/1934 | Bryan .......................... 239/44 |
| 4,477,414 A | | 10/1984 | Muramoto et al. |
| 5,000,383 A | | 3/1991 | Van Der Heijden |

FOREIGN PATENT DOCUMENTS

| | | |
|---|---|---|
| DE | 44 33 954 | 3/1996 |
| EP | 62119322 | 11/1988 |
| FR | 747 069 | 2/1932 |
| JP | 2144112 | 6/1990 |
| WO | WO 94/29650 | 12/1994 |
| WO | WO 98/28161 | 7/1998 |

* cited by examiner

Primary Examiner—Robert A. Hopkins
(74) Attorney, Agent, or Firm—Pillsbury Winthrop LLP (57) ABSTRACT

Dispensers of volatile liquids have a liquid reservoir (10) feeding a downwardly extending dispersal screen (2) formed by spaced threads or groups of threads (20) down which the liquid (L) flows as it is vaporised the screen having a large thread; void ratio whereby a relatively small quantity of liquid is exposed, so that the liquid on the screen is constantly replaced. In other dispensers utilizing a downwardly extending dispersal screen (30; 42; 82; 110; 120; 160). a capillary wick (38; 52; 94; 140; 172) leads the liquid upwards from a reservoir (34; 50; 92; 136; 166) to produce a syphon effect. The amount of liquid on the screen (160) may be limited by an arrangement (184; 186) for interrupting the syphon flow. The liquid flow to a dispenser screen (42; 82; 110) may also be regulated by taking liquid from a supply container (48; 90; 108) into a reservoir chamber (50; 92; 136) having a constant liquid level, whereby the rate of liquid flow is independent of the level in the supply container. Dispensers according to the invention may have any one or more of these features.

27 Claims, 6 Drawing Sheets

VOLATILE MATERIAL DISPENSERS

This application is the National Phase of International Application PCT/GB99/03938 filed Nov. 25, 1999 which designated the U.S. and that International Application was published under PCT Article 21(2) in English.

This invention relates to dispensers for volatile materials in liquid form, in particular for releasing such materials into the surrounding atmosphere.

The release of volatile liquids, e.g. of air freshening materials and fragrances, into the atmosphere over a period of time can be achieved in a number of ways. Where a slow sustained dispersal of the material is required, it is known to expose a porous pad impregnated with the material or to provide a liquid reservoir from which a wick protrudes to draw up liquid from the reservoir, the liquid then evaporating from the exposed surface of the wick. These known dispersal methods have the advantage of low cost but they have a failing if the material to be dispersed is a mixture of substances with different volatilities, as is typical of fragrances. The components with greater volatility then escape more readily than those with lower volatility with the result that the character of the fragrance changes markedly over the period of use, which is clearly undesirable. If an impregnated porous pad is used, there is the further disadvantage that it cannot be readily seen when the volatile material is about to be exhausted.

According to one aspect of the present invention, there is provided a dispenser for a volatile liquid comprising at least one dispersal screen in which a series of threads run in one direction with spaces between at least some of the threads, a liquid reservoir in communication with the screen, the individual threads and/or closely grouped pluralities of threads of said series between said spaces being arranged to exert a capillary action on liquid reaching the screen from the reservoir.

Such a dispersal screen is able to offer a generally laminar and permeable base over which a material to be released can readily diffuse, e.g. by capillary action. The spaces between said threads increase the exposure of the liquid to the surrounding atmosphere and allow a flow of air to be induced through the screen to increase the rate of dispersal. Preferably, said spaces are at least equal to the thickness of the threads or groups of threads, and to enhance these effects it can be arranged that said spaces are equal to several times that thickness.

The screen can have a very low bulk in comparison to the area exposed to the atmosphere so that the amount of liquid taken up from the reservoir onto the screen at any moment is limited and is relatively quickly dispersed. It can therefore be arranged that the rate at which the components with higher volatility are exposed is restricted, as compared with a prior art pad, while less opportunity for components with lower volatility to accumulate on the screen, whereby a more even dispersal of the liquid over a period of time can be achieved.

In a preferred form of screen, said series of threads is interwoven with a second series of threads running transversely thereto, the threads of said second series being spaced so as to provide a void ratio transverse to the direction in which they run that is preferably at least as great as that provided by the spaces between the threads or groups of threads of the first series.

According to a further aspect of the present invention, there is provided a dispenser for a volatile to material comprising a reservoir for containing the material as a liquid, and a dispersal screen from which the material can evaporate or volatilise into the surrounding atmosphere, said screen being in communication with the liquid in the reservoir and comprising a fabric having first and second series of threads running in mutually transverse directions, at least in one of said directions the threads being arranged in spaced groups in which the threads of a group are more closely spaced than in the spaces between the groups, said groups of threads being arranged to exercise a capillary action an the liquid reaching the screen from the reservoir to promote diffusion of the liquid over the screen.

The screen can be arranged with threads dipping into the liquid in the reservoir to draw the liquid over the screen surface. There can however be advantages in employing an intermediate transfer device, e.g. a member providing a plurality of capillary passages such as a wick, to take up the liquid from the reservoir and carry it to the screen. Preferably, the transfer device is shielded from exposure to the atmosphere, to ensure that there is no significant volatilisation of the liquid before it reaches the screen.

The screen can be mounted in a rigid surrounding frame. It can be composed of more than one layer having said series of threads, but if there are a multiplicity of layers it is desirable to ensure that their combined effect does not unduly impede air flow through the screen, in order to limit the time between the liquid reaching the screen and it being released into the surrounding atmosphere. It is also possible to supply a plurality of dispersal screens from a common reservoir.

It is generally desirable to employ gravitational effects to complement capillary forces acting on the liquid, the liquid thus being supplied to the upper region of a downwardly extending screen. Such an arrangement can give a more even spread of liquid over the screen, so enhancing the rate of evaporation. The screen may be so arranged that the gravitational forces produce a syphon effect drawing the liquid from a reservoir below the top of the screen onto the top of the screen. Although capillary forces may be relied on to draw the liquid onto the screen, once the syphon effect has been established and the flow path onto the screen has become saturated, the capillary effect will cease to have any influence. Flow is continued through the action of intermolecular and gravitational forces until the liquid path is broken. In addition, by locating the bottom of the screen below the liquid level in the supply reservoir a hydrostatic bias can be established that ensures the flow is maintained.

Thus, according to another aspect of the invention, there is provided a dispenser for a volatile liquid comprising a reservoir for the liquid and a fluid conduit providing a flow path extending upwardly from the reservoir to an upper region of a downwardly extending laminar dispersal or diffusion screen, said fluid conduit having means for drawing liquid from the reservoir to said upper region to allow the liquid to flow by gravity down the screen as it is dispersed therefrom.

The laminar screen is preferably of a form that holds only a small amount of liquid at any instant, for example having the structure described above, although other screen materials may be employed. Under optimum conditions it may be arranged that the liquid will disperse completely from the screen before it reaches the bottom of the screen. In practice, however, it may be desirable to provide a lower marginal region with a greater liquid absorption capacity than the higher regions of the screen, to hold any surplus of liquid that has not volatilised before reaching the lower region. Liquid can thus be retained in the lower region in adverse operating conditions, for example if there is a drop of temperature below the average, as it disperses more slowly.

Additionally or alternatively the surplus liquid can be arranged to be transferred to a further dispersal element. In these ways, lower volatile components can be drawn off the main area of the screen so as not to block the flow of higher volatility components onto the screen.

If a dispenser according to the invention has a fluid circuit which provides an upwardly extending flow path from a reservoir of liquid to be dispersed to the top region of a screen to allow the liquid to be exposed to the surrounding atmosphere as it flows down the screen, it may be arranged that the liquid level in the reservoir is maintained substantially constant to give a more uniform conditions along the liquid path to the top of the screen.

In one arrangement having this characteristic, the dispenser may comprise a reservoir chamber for the liquid having an opening to the atmosphere and located below a container having a bottom outlet below the level of said opening for supplying liquid to the reservoir chamber, in the reservoir chamber an outlet conduit extending from a level below said container outlet for leading liquid from the chamber to the screen, whereby lowering of the liquid level in the chamber below said level of the supply container bottom outlet by the removal of liquid through said conduit allows further liquid to flow from the container into the chamber to maintain the liquid level therein.

The reservoir chamber may be supplied by a liquid container in the form of a replaceable sealed container, and means may be provided for placing the container in communication with the chamber automatically as it is mounted in place on the dispenser. Thus, a piercing element may project upwardly from the chamber, into a socket into which the supply container is sealingly inserted, the bottom of the container being pierced as it is inserted.

In an alternative embodiment, a refillable supply container is provided. If it is open to atmosphere during the filling, means are required to prevent the liquid simply flowing through the container and draining from the bottom outlet into the reservoir. In one preferred form, the container is provided with coupled inlet and outlet valves by means of which, when the inlet valve is opened to allow filling, the outlet valve is automatically closed to seal the supply container from the reservoir.

As an alternative to attempting to maintain uniform supply conditions to the screen, or in addition thereto, it may be arranged that the amount of liquid on the screen determines the supply of further liquid to the top of the screen, so as to limit the amount on the screen at any instant. This may be a preferred method of operation if there are significant fluctuations in the rate of dispersal from the screen, e.g. due to changes of ambient temperature. In particular, the amount of liquid held by the screen at any moment may be limited by providing an arrangement that interrupts the supply of further liquid to the screen in dependence upon the amount already present, Thus, in one form of such an arrangement, the screen is displaceably supported in a manner allowing it to move in dependence upon the weight of liquid it holds, such that said movement displaces the screen to interrupt the fluid conduit flow path when the weight exceeds a permitted maximum. If liquid continues to disperse from the screen after the flow path has been interrupted, the screen can return to its previous position when it has been sufficiently lightened, and it can be arranged that the return displacement re-establishes the flow path, so that the supply of liquid to the screen begins again.

This process can be accelerated by removing excess liquid from the screen. For example, an absorbent holding element may be located adjacent the screen to come into contact with said lower region when the screen is displaced by the weight of excess liquid. Some of the liquid in the lower region of the screen can then flow onto the holding element, which may itself be in the form of a sheet or mat providing a dispersal surface from which the liquid can volatilise, albeit more slowly. With a fragrance having a mixture of constituents of different volatilities, the accumulated liquid will usually consist wholly or mainly of the less volatile constituents, and the removal of this liquid with re-establishment of the flow of fresh liquid to the screen ensures continuance of the supply of the more volatile components so that the sensed character of the fragrance is maintained more uniform.

Embodiments of the invention will be described by way of example with reference to the accompanying drawings, in which:

FIG. 1 illustrates a part of a dispenser according to the invention to an enlarged scale, FIGS. 2 and 3 illustrate some details of the construction of the dispenser in FIG. 1, FIGS. 4 and 5 illustrate another dispenser according to the invention incorporating the screen structure of FIG. 1, the liquid flow pattern being shown in FIG. 5, FIG. 6 shows a further example of dispenser according to the invention, each with the outer casing partly broken away, FIGS. 7 and 8 are schematic front and side views respectively, illustrating further a feature of the dispenser of FIG. 6, FIG. 9 shows another example of dispenser according to the invention with the outer casing partly broken away, FIGS. 10 and 11 are schematic front and plan views of a particular form of dispersal screen that can be used, for example, in the dispenser of FIG. 9, FIGS. 12 and 13 are schematic front and side views of another form of dispersal screen for a dispenser according to the invention, FIG. 14 is a side view of a further dispenser according to the invention, FIG. 15 is a front view of the dispenser of FIG. 10 with the reservoir chamber removed, FIG. 16 is a fragmentary schematic view of one of the screens for the dispenser of FIGS. 10 and 11, FIGS. 17 and 18 are plan and front views respectively of yet another dispenser according to the invention.

Ref erring to FIG. 1, a fabric screen or curtain 2 depends from a tubular support 4, an upper edge of the screen being inserted into a slit 6*a* (FIGS. 2 and 3) cut in the bottom face of a horizontal limb 6 of the support. After insertion, the edges of the slit grip the screen tightly to give a liquid-tight seal around the inserted edge. From the horizontal limb 6, a vertical limb 8 of the support extends into a closed liquid container 10 providing a reservoir of a volatile liquid L such as a fragrance. Within the hollow interior of the support 4 a wick 12 provides a communication path for liquid flow between the container and the top of the screen, sealed otherwise from the exterior.

FIG. 2 shows how the top of the screen is placed in intimate contact with the wick to take up liquid from the wick. FIG. 3 shows the slit 6*a* in the limb 6 of the support formed as a simple cut, before insertion of the screen edge. The resilience of the tubular limb causes the edges of the cut to grip the screen sealingly when it has been inserted, and to facilitate insertion it is possible to form a small entry notch 6*b* at one end of the slit.

The liquid L is drawn into the wick 12 by capillary action and a vent 14 is provided in top cap 16 of the container to allow air to enter to make up for the liquid lost. The wick 12 carries the liquid into the horizontal limb 6 of the support to distribute it across the top edge of the screen.

Figure 1:
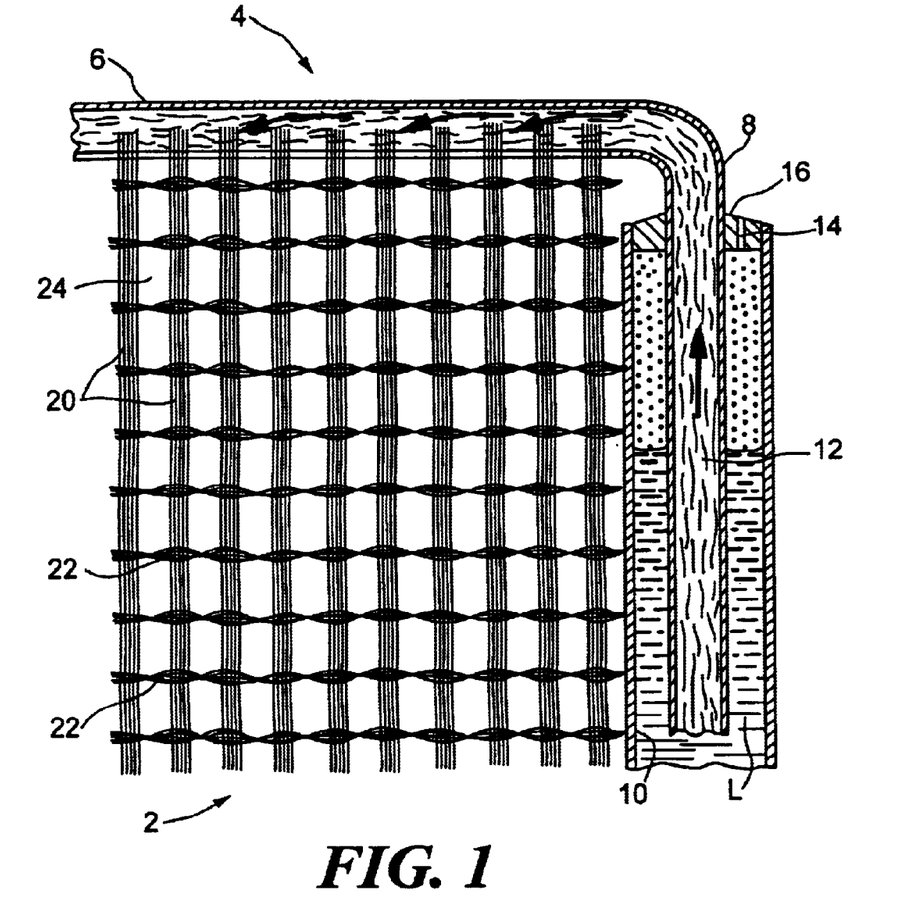
Figure 2:
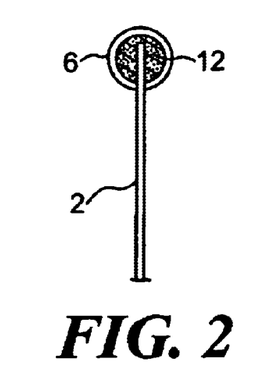
Figure 3:
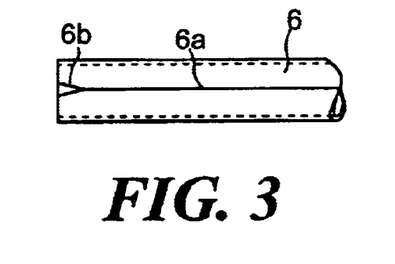

The fabric of the screen shown in FIG. 1 is composed of polyester fibres which comprise a first vertical series of warp threads 20, each warp thread formed by bundles of generally straight polyester mono-filaments, interwoven with a second series of weft threads 22 of the same material running horizontally. The thickness of the warp threads 20, which is effectively the thickness of the screen, is approximately 0.25 mm. The warp threads 20 are arranged into groups with spaces 24 between the groups of threads many times wider than the bundles of filaments forming the threads.

More generally the width of the spaces 24 is at least equal to the thickness of the groups of threads and is preferably at least equal to twice that thickness. There are fewer filaments in the weft threads 22 than warp threads 20, and the groups of threads may be more widely spaced, so that the fabric has a greater thread: void ratio in the vertical direction than in the horizontal direction.

The closely spaced surfaces of the filaments of each warp thread form capillary passages for liquid reaching their upper ends in the tubular support 4. The liquid is therefore drawn along the warp threads through the main body of the fabric, the flow being assisted by gravity and hydrostatic pressure. Because of the open weave nature of the fabric, the liquid is exposed widely to the surrounding atmosphere and evaporates readily from the screen as it travels along it. The weft threads 22 will also exert some capillary action, further increasing the exposure of the liquid to the atmosphere.

The open weave of the screen fabric also has the effect that the bulk of the screen material can be kept small in relation to the screen area, with the result that only a small quantity of liquid will be present on the screen at any instant. It thus acts as an emanator rather than a reservoir for the volatile liquid. As evaporation occurs, the screen is quickly replenished with fresh liquid so reducing the risk of less volatile components of a fragrance accumulating to the extent that the balance of the fragrance being released to the atmosphere varies undesirably over a period of time. The quantity of liquid on the screen is also limited by the use of non-absorbent fibres in the present example for the screen material, so that the liquid is confined to the surfaces of the fibres, from where it is of course better exposed to the surrounding atmosphere.

The rate of flow is also dependent on the viscosity of the liquid, so that the flow will increase with increase of temperature. However, volatility will also increase with temperature, so these two influences tend to counteract each other to stabilise the quantity of liquid on the screen at any time.

If desired, a greater rate of evaporation can be induced by introducing a flow of air through the screen. A relatively large rate of air flow can be easily generated with little pressure loss because of the open weave of the fabric. In one possible application of the invention, the screen is located in the path of an intermittently operated fan in order to release pulses of fragrance at intervals, so giving an enhanced perceived effect.

Heating will also increase the rate of evaporation, and a black screen will enhance the effect of any heating. By the use of appropriate heat sources it is possible to induce convection flows over the screen to augment the rate of evaporation.

Figure 4:
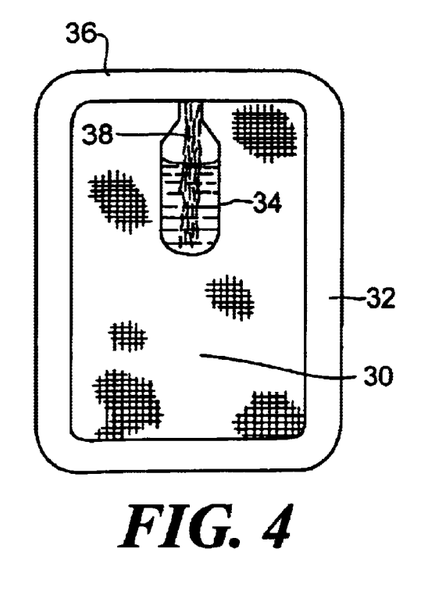
Figure 5:
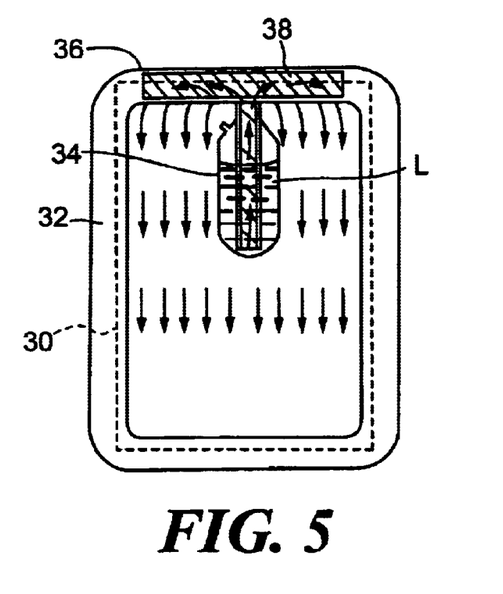

FIGS. 4 and 5 illustrate a volatile liquid dispenser that also uses the screen material shown in FIG. 1. The screen 30, the boundaries of which can be seen in FIG. 5, is held around its periphery in a slit in a surrounding tubular frame 32. A transparent container 34 providing a reservoir of volatile liquid L depends from the middle of the top horizontal limb 36 of the frame. A T-form wick 38 extends from the bottom of the container into the top limb 36 to both sides of the container, terminating a little short of the side edges of the screen, to spread the liquid drawn from the container across the width of the screen. The release of the volatile liquid from the screen occurs in the manner already described with reference to FIG. 1, as indicated by the arrows in FIG. 5. It will be noted that the transparent container provides a ready indication of when the dispenser is nearing exhaustion. It can be arranged that the liquid container of the dispenser is to be replenished or replaced when the liquid is exhausted, or the dispenser may be produced in disposable form as it can be made at relatively low cost.

Although the preceding examples, and some of those described below, show the top of the screen in contact with a separate wick, if a suitable screen material is employed it is possible at the top of the screen to roll the material into a closely packed cylinder or to fold it into a thicker hem, so that it forms its own wick, or to form it around a thinner wick.

The position of the container in relation to the vertical extent of the screen has an influence on the transfer of liquid to the screen because the level of the reservoir of liquid in the container determines the hydrostatic pressure along the fluid path that extends through the wick and along the screen. Points at the same level on that path have the same hydrostatic pressure, as in a syphon, so the higher the container the greater will be the flow onto the screen. Once the screen has become saturated by the driving effect of the hydrostatic forces acting in this manner, and complemented by the intermolecular forces along the liquid path, capillary action will cease to operate. The potential influence of hydrostatic effects can be employed in the operation of a dispenser according to the invention to change the rate of flow by adjusting the relative positions of the container and screen, which may require no more than a reorientation of the dispenser.

Figure 6:
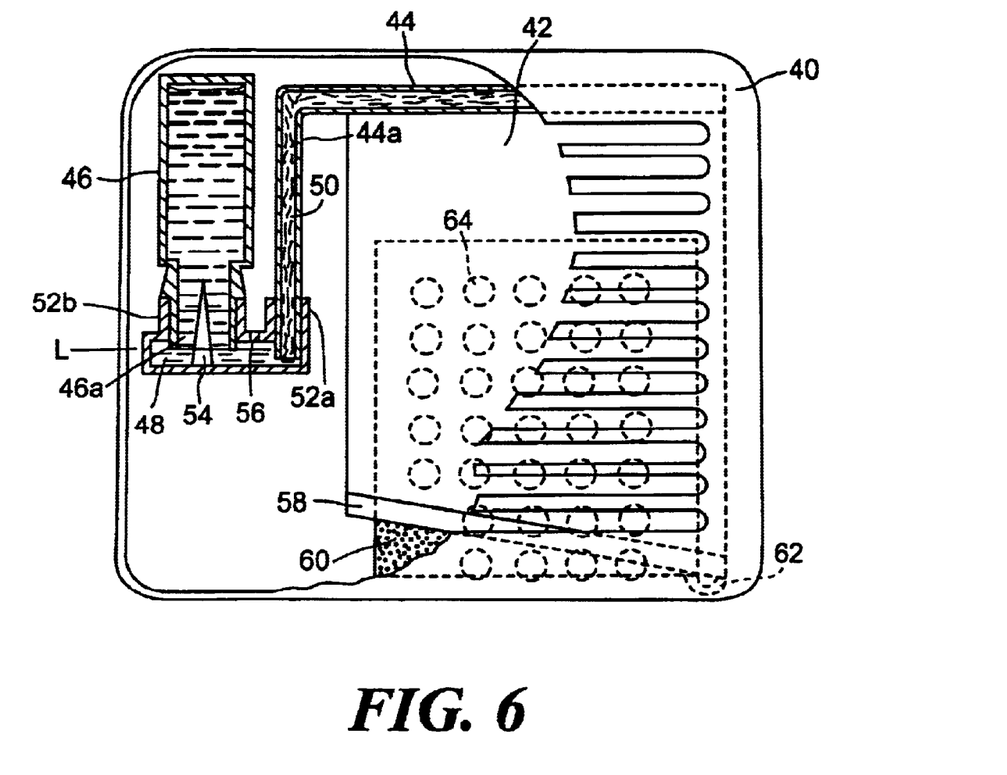

FIG. 6 illustrates an embodiment of the invention in which the level of the reservoir of liquid feeding the screen is kept constant, so that a constant hydrostatic pressure is maintained. Within a protective outer casing 40 having grid-like faces to allow free air circulation, a screen 42 of the same form as the preceding embodiments is suspended from a top support 44. A replaceable sealed liquid capsule 46 supplies the volatile material to a fixed level reservoir chamber 48. The chamber 48 is in fluid communication with the top of the screen through a wick 50 scaled within an angled tubular enclosure formed by the top support 44 and a vertical extension 44a continuing from that support, plugged into a socket 52a in reservoir top wall. The liquid container is plugged into a further socket 52b of the reservoir chamber 48 and as it is inserted a spike 54 projecting upwards from the reservoir chamber pierces bottom seal 46a of the container. A groove (not shown) in the spike then allows liquid to flow from the container into the chamber 48 which is maintained at atmospheric pressure by a vent 56. The liquid in the reservoir chamber is taken up through the substantially sealed wick 50 to the screen.

Initially, the bottom of the capsule 46 is above the liquid level in the reservoir chamber 48 and air can enter the capsule to replace liquid falling into the chamber. After the liquid level in the chamber has risen sufficiently to seal the exit from the capsule, however, further outflow will cease as a partial vacuum is created in the capsule. The flow will begin again only as the level in the chamber 48 is reduced by the uptake of liquid through the wick. In operation, therefore a point of balance can be reached in which the liquid level in the reservoir chamber 48 remains substantially constant. The syphon effect in the wick and screen therefore also remains substantially constant.

The level of the liquid in the reservoir chamber 48 determines the hydrostatic pressure in the liquid on the screen 42, since there is a continuous column of liquid between the reservoir and the screen. The reservoir chamber 48 is positioned intermediate the height of the screen. This ensures there is a positive hydrostatic pressure driving the liquid down the lower region of the screen and so stimulating the flow down the screen from the top support 44.

An optimum vertical length of screen would ensure that the volatile material could be completely dispersed into the atmosphere before it reaches the bottom of the screen. However, variations in the operating conditions may make it impossible to satisfy this condition always. For example, if the liquid includes components of low volatility, which may be required as carriers or extenders, for the active components, for example, the capillary action and gravity will act to carry such materials towards the bottom of the screen. This reduces any tendency these materials may have to clog the main area of the screen to the extent that the entry of fresh liquid to the screen is significantly impeded.

However, because fragrances will commonly have components of lesser volatility ("low notes"), means are preferably provided at the bottom of the screen to take up and dissipate any excess liquid reaching there. For this purpose, at its bottom edge the screen 42 has a thicker hem 58 formed by folding the screen material back on itself. The hem is inclined downwards at a small angle away from the liquid supply side. Also, at its lower end the hem 58 is connected to an absorbent cellulose pad or mat 60, behind and parallel to the screen, through a capillary link 62 which provides a limited cross-section flow path.

Any low volatility component of the liquid that has not been evaporated while flowing down the screen will therefore run off through the capillary link to the pad which has a much greater liquid holding capacity than the screen. Although as already indicated any low volatility components remaining may be largely non-aromatic, so their failure to vaporise rapidly will not in itself significantly affect the fragrance perceived, it is desirable to remove them from the screen in order to ensure that the maximum screen area is available for the continuing flow and dissipation of the more volatile components of the liquid.

The limited cross-sectional area of the link flow path regulates the rate at which liquid will transfer to the larger liquid-holding capacity of the pad. To improve its ability to disperse the fluid it holds, the pad may be provided with holes 64 (only partly illustrated) or other formations increasing its surface area.

Figure 7:
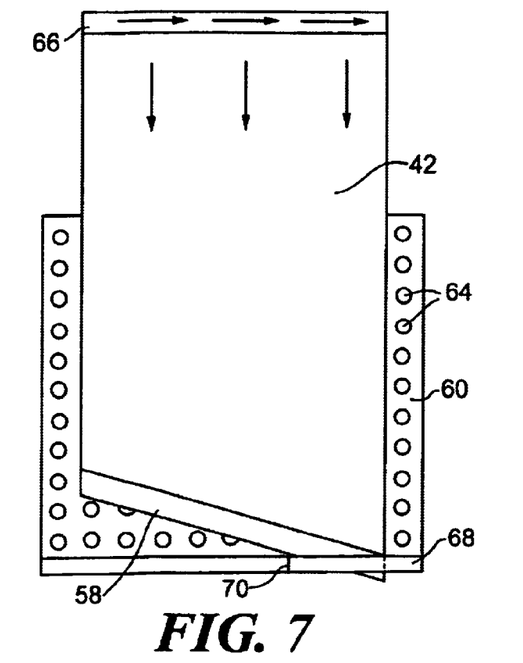
Figure 8:
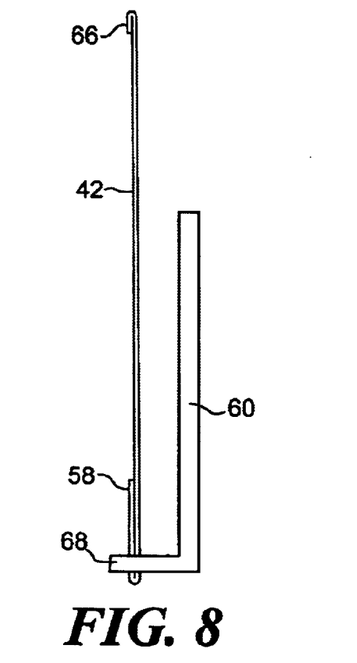

FIGS. 7 and 8 are further illustrations of the combination of dispersal screen and absorbent pad as employed in the example of FIG. 6 and corresponding parts will be designated by the same reference numbers. The screen material is folded over at the top to form a hem 66 that can complement the wick 50 or substitute for its horizontal limb. The screen 42 and pad 60 are connected together at the bottom of the screen by forming a lip 68 on the bottom edge of the pad to project into the plane of the screen and inserting the lowermost tip of the screen hem 58 into a slit 70 in that lip. The small contact area between the hem and the tip prevents an excessive rate of flow of liquid onto the pad.

Different materials can be employed from the screen of a dispenser according to the invention. Thus, while the illustrated example described above shows bundles of non-absorbent mono-filaments forming the warp threads along which the liquid travels, it is also possible to form the threads from staple fibres, whether of synthetic or natural fibres. Nor do the warp threads necessarily have to be interwoven with transverse weft threads. Alternatively, it is possible to employ a relatively closely woven fabric as a dispersal screen, although increasing the liquid-holding capacity of the screen unduly at the expense of reducing exposure to the surrounding atmosphere can adversely affect performance.

Figure 9:
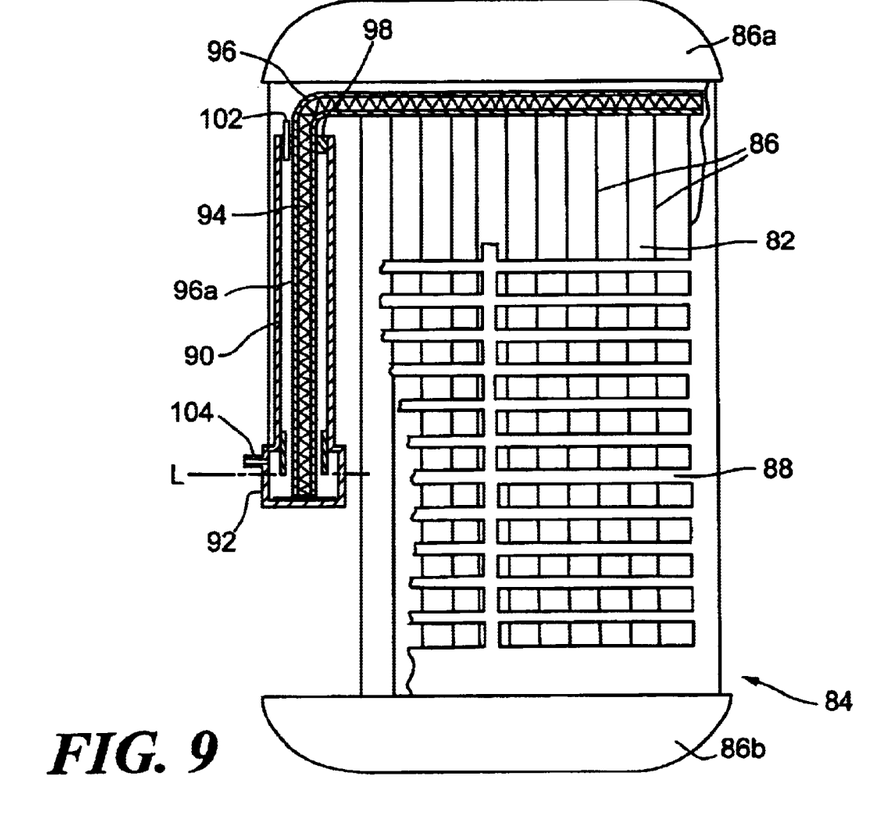
Figure 10:
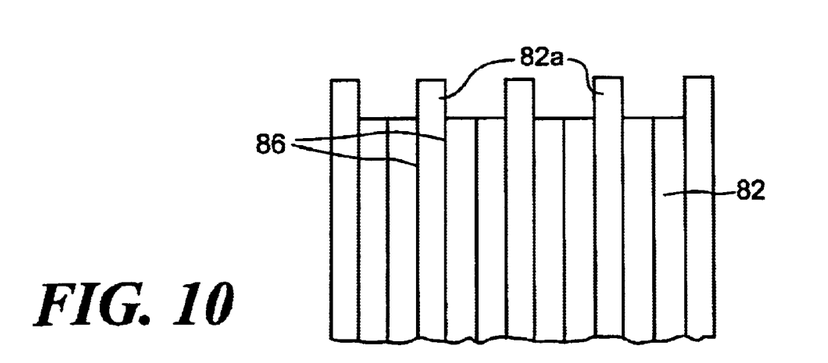
Figure 11:
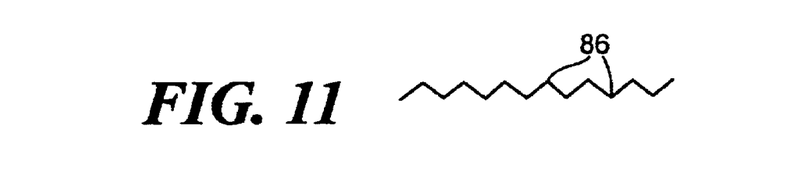

FIGS. 9–11 illustrate another form of dispenser according to the invention using a screen 82 which may be of similar material to the preceding examples, or of staple fibres as just mentioned.

The screen is enclosed in a protective casing 84 having, between top and bottom caps 86a, 86b, grid-like walls 88 to give both faces of the screen maximum exposure to the surrounding atmosphere. Within the casing to one side of the screen 82 is an elongate tube forming a liquid supply container 90 for the material to be dispensed to the screen through a wick 94. Although not shown, as in the preceding example, an absorbent pad can be connected to the bottom of the screen to draw off any low volatility liquid tending to collect there.

The container 90 supplies the liquid to a fixed level reservoir chamber 92 which regulates the flow. The liquid is taken up by the wick 94, which in encased in an L-form tube 96. The tube 96, comprises a vertical limb 96a which extends from the reservoir chamber, through the container 90 and emerges through a top seal 98 of the container. The wick 94 is thus exposed to the liquid only at its lower end, where its encasing tube 96 extends close to the bottom of the reservoir chamber 92. The supply container 90 also extends some distance downwards into the chamber 92 but terminates above the level of the wick tube 96.

The container is filled initially through a filling tube 102 which is then sealed. The reservoir chamber 92 is initially sealed from the atmosphere, but to activate the device an air vent 104 between the top of the chamber and the bottom of the reservoir 90 is opened, so that atmospheric pressure is established in the chamber in order to regulate the flow through it. In the illustrated example, the vent 104 is provided by a closed tubular plug which can be opened by severing its protruding tip. Liquid can then flow down from the supply container 90 into the chamber 92 and be replaced by incoming air, until the bottom of the container is sealed by the liquid in the reservoir chamber. As liquid is drawn from the chamber to the screen by the wick 94, further liquid is able to flow from the container 90 to maintain the liquid level L in the chamber 92 substantially constant. The height of the liquid in the supply container 90 therefore does not affect the rate of liquid transfer to the screen 82. The height of the reservoir 90, as in the preceding example, is chosen to give a positive hydrostatic pressure in the lower region of the screen.

To increase the surface area exposed to the atmosphere, the screen 62 is pleated, FIGS. 8 and 9 showing, to the same scale, the width of the screen before and after the pleat folds have been made. FIGS. 8 and 9 show vertical fold lines 86 forming the pleats, but the screen can alternatively be pleated transversely in a similar manner. It is also possible to configure the screen in other ways to increase the surface area.

In the example illustrated in FIGS. 9 to 11, as in earlier examples, the top of the screen is inserted into a substantially sealed slit in a horizontal limb 96a of the wick tube to lie in contact with the wick 94 for the transfer of liquid to the screen 82. FIG. 10 shows portions of the pleats cut away at the top of the screen to make it easier to insert the remaining tab-like portions 82a into a linear slit (not shown) cut in the horizontal limb which then seals around the portions if the wick tube 76 is made of a suitably elastic material.

If desired, filling can be performed under pressure, so that some liquid is forced into the wick 94 before the constant level reservoir chamber 92 is opened, so increasing the total charge of liquid. Conveniently, the filling tube 102 is of thermoplastic material, which can be simply heat sealed when filling has been completed.

The open faces formed by the grid-like walls 88 of the casing 84 also expose the tubular supply container 90 to view. If the tube material is transparent or translucent, the use of the liquid can thus be continuously monitored. The horizontal grid bars of the walls 88 then act as convenient scale markers of the filling state of the reservoir.

Figure 12:
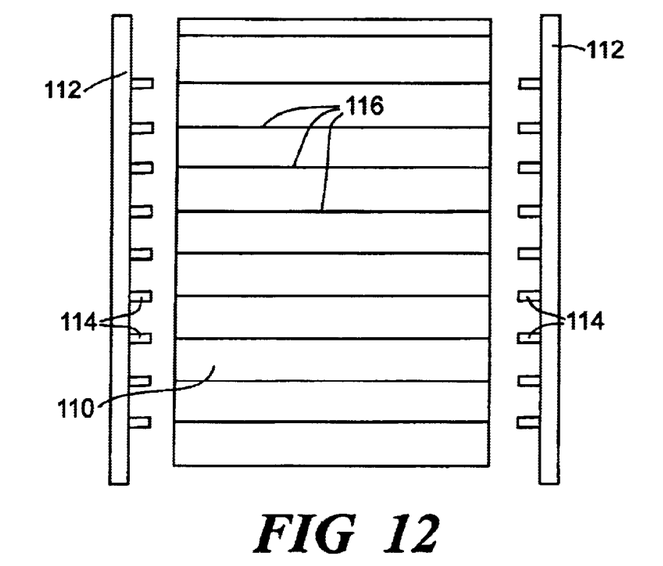

As an alternative to the vertically pleated screen of FIGS. 9–11, FIGS. 12 and 13 illustrates a horizontally pleated screen 110 that can be employed in a dispenser according to the invention. FIG. 12 shows the screen 110 and opposite side supports 112 having a series of pegs 114, which are assembled with the screen so that the walls of the supports 112 lie close to but out of contact with the edges of the screen and the pegs 114 project a short distance into the folds 116 of the pleats to maintain them in place.

Figure 13:
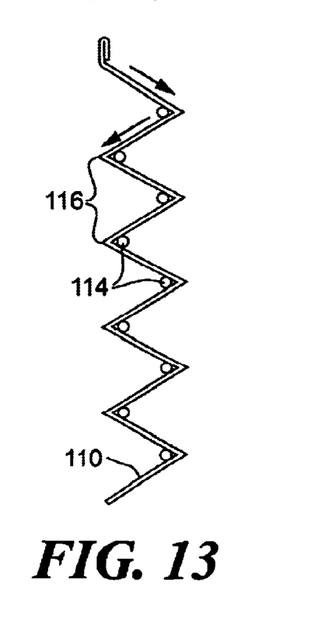

By forming the screen 110 with a convoluted form in side view, as in this example, the liquid path length can be increased for a given height of screen and the inclined faces of the pleats reduce the effect of gravity on the flow of the liquid. The liquid thus flows more slowly and is exposed over a larger area.

An absorbent pad (not shown) can be connected to the bottom of the screen, in the manner already described, to draw off any liquid accumulating at the bottom of the screen. In this instance it may be in contact with most or all of the width of the screen.

Figure 14:
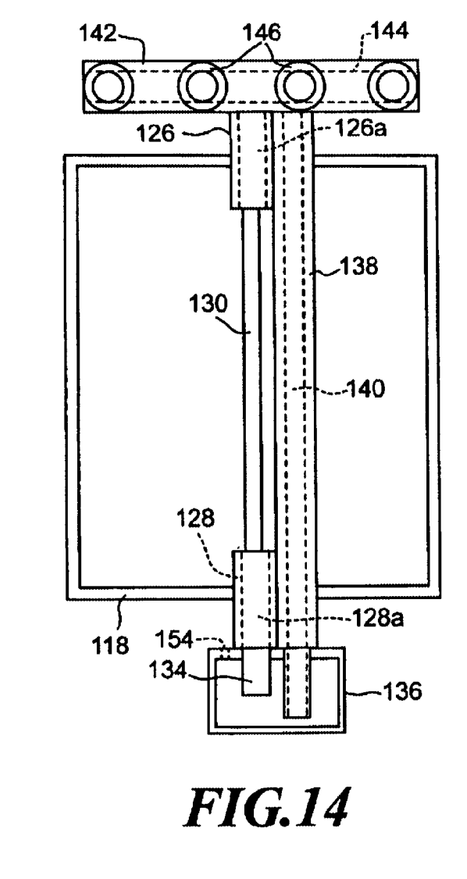
Figures 15, 16:
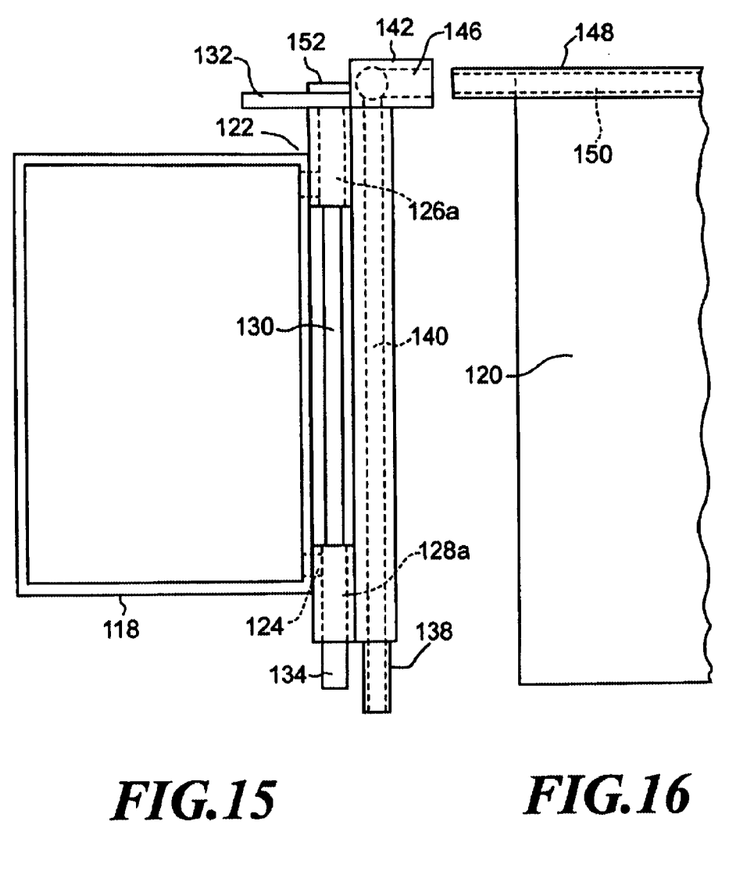

FIGS. 14–16 illustrate a further form of dispenser according to the invention in which a refillable supply container 118 supplies multiple screens 120 (FIG. 16), the latter being indicated only in outline as they can be constructed generally as described with reference to any of the preceding examples.

The container 118, here shown as a rectangular vessel, has inlet and outlet ports 122, 124 at the top and bottom of one side wall, the ports being provided with inlet and outlet cocks 126, 128 respectively. In each cock is a rotary cock body 126a, 128a, both bodies being fixed to a coaxial shaft 130 to which can be rotated by a control lever 132 rigidly connected therewith. The cocks can thereby be rotated together between a filling position in which the inlet cock 126 is open and the outlet cock 128 closed, and a dispensing position in which the inlet cock 126 is closed and the outlet cock 128 is open.

The outlet cock 128 has a hollow bottom spigot 134 through which it opens downwards into a constant level reservoir chamber 136 below the container 118. The spigot terminates some distance below the top of the chamber, but above the bottom of a vertical wick tube 138 encasing a main supply wick 140. The other end of the wick tube joins a horizontal outlet manifold 142 in which an interconnecting wick 144 is held in contact with the vertical supply wick 140. Sockets 146 at intervals along the manifold 142 receive supply wick 148 tubes at the tops of the respective screens 120. The supply wick tubes 118 plug into the manifold in a fluid-tight manner to place the screen supply wicks 150 within them in contact with the inter-connecting wick 144 so as to complete substantially sealed liquid flow paths from the constant level reservoir chamber 136 to the respective screens 120. The manifold 142 can take any configuration required to give a desired spacing of the screens.

Initially, with the inlet cock 126 open and the outlet cock 128 closed the supply container 118 can be filled through filler opening 152 and the cock 126. The shaft 130 is then rotated to close the inlet cock 126 and seal the container 118 from the atmosphere, and simultaneously open the outlet cock 128. An air vent connection 154 maintains atmospheric pressure in the constant level reservoir chamber 136, so that liquid now flows from the container through the cock 128 to fill the chamber to the level of the bottom of the spigot 134. In the same manner as described for the previous example, the constant level chamber 136 is automatically replenished as liquid is drawn off by the wicks 130, 144, 150 to be evaporated from the screens 120. When the supply container is to be replenished, as the control lever 132 is pivoted to open the inlet cock 126 the outlet cock 128 is simultaneously closed.

The supporting frames of the screens 120 are not shown but they may be constructed in a similar manner to the earlier described examples. The screens themselves may incorporate any of the features described in the screens of the preceding examples, The number of screens in use can be varied, the surplus sockets not in use then being plugged closed.

Figure 17:
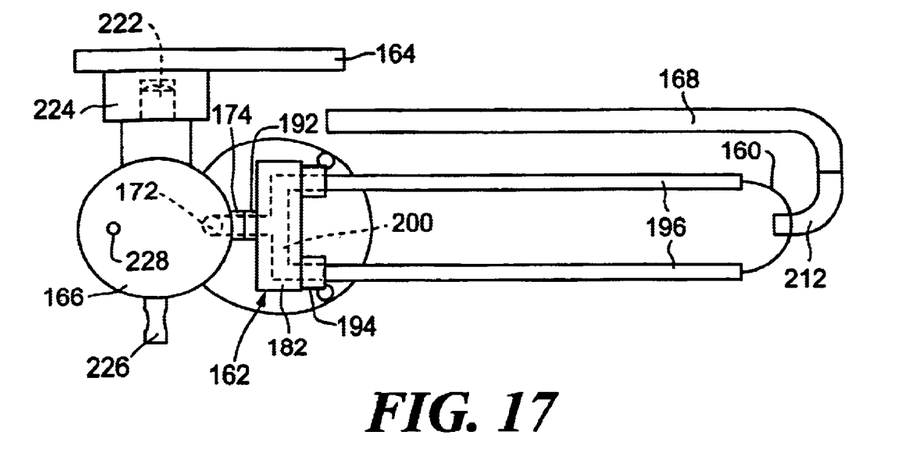
Figure 18:
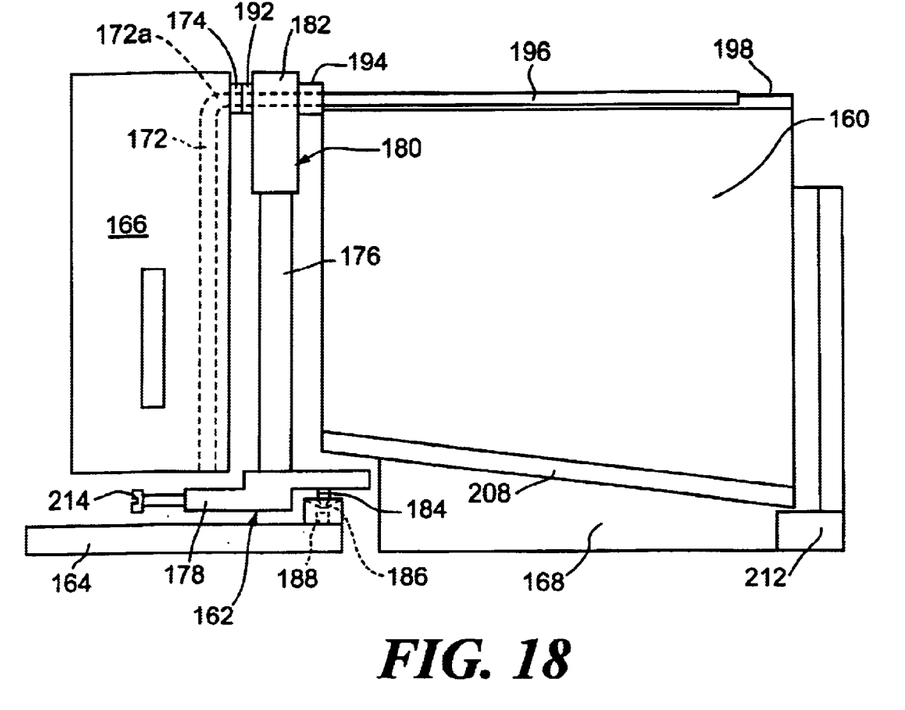

FIGS. 17 and 18 illustrate a further dispenser according to the invention which has a mechanism that regulates the supply of liquid to limit the amount held by dispersal screen 160 at any instant. The screen is folded on itself in a U-shape plan form to increase the surface area, and is mounted on a carriage 162 that is pivotally balanced in the dispenser outer frame 164, shown only fragmentarily in the figures. The screen 160, which may be of a form described with reference to any of the earlier embodiments, is supplied from a reservoir 166 in a fixed position on the frame 144. Mounted on the frame 164 separate from the screen is a transfer pad or mat 168 of absorbent material to which surplus liquid on the screen can be transferred so that.it will not block the flow of fresh liquid down the screen.

As in the earlier examples, a wick 172 extends from the bottom to top of the reservoir and at its upper end it continues as a horizontal extension 172a filling a hollow spigot 174 projecting from the main body of the reservoir. The end face of the wick extension 172a is exposed and is coplanar with the end face of the hollow spigot 174 in which it is encased.

The carriage 162 has a frame structure comprising a vertical mast 176 at the lower end of which is a transverse lower limb 178 and at the upper end of which is a bracket 180 having within its upper region a fluid manifold 182. The lower limb 178 is provided with a pair of steel bearing points 184 which locate in a pair of seats 186 in a lower region of the outer frame 164. The points are retained in the V-form upper faces of the seats 186 by magnets 188.

From one side of the fluid manifold 182 a hollow spigot 192 projects to confront and abut against the spigot 174 of the reservoir 166. From the opposite side of the manifold 182 a pair of sockets 194 project to hold a pair of support tubes 196 from which the U-form dispersal screen 160 is suspended. In the manner described in earlier examples, the support tubes 196 have slits (not shown) in their lower faces through which the upper margin 198 of the straight limbs of the U-platform screen is inserted. The screen upper margin 198 is in the form of a rolled or folded hem held within the 
support tubes to form a distributing wick for the curtain. The manifold 182 contains a branched wick 200 which at the one side extends to the end face of the hollow spigot 192, and at the opposite side has two branches in close contact with the ends of the curtain upper margin 198 in the support tubes.

The carriage 162 is shown balanced on the seats 186 with the reservoir and manifold spigots 174, 192 in contact, so that the wicks they each contain are also in contact to complete a continuous path for liquid from the reservoir 166 to the screen 160. The screen has an inclined bottom margin 208, like the upper margin 198 made thicker by rolling or folding the screen material. At the lower edge of the transfer pad 168 a portion of the pad forms an extension 212 from its main area projecting under the lowermost end of the inclined bottom margin 208 of the screen. In the illustrated state, with the spigots 174, 192 in contact, there is a spacing between the mat extension 212 and the screen lower margin 208.

The carriage maintains its illustrated state if the centre of gravity of the weight supported by the seats 186 is located to the left of a vertical plane through the bearing points 184, as seen in FIG. 18. The position of the centre of gravity is dependent upon the amount of liquid held on the screen 160 and it is arranged that when sufficient liquid has accumulated on the screen, the carriage 162 will tilt clockwise on its bearing points. The contact between the wicks 172a, 200 in the spigots 174, 192 is then broken, so interrupting further fluid flow to the manifold 182, and the screen drops, so that the bottom margin 208 comes to rest on the mat extension 212.

An adjustment screw 214 on the carriage 162 can be turned to regulate when this tilting occurs, ie. to set the maximum amount of liquid that the screen should hold. Normally, clockwise tilting is arranged to occur once the screen has become saturated and some liquid has accumulated in its bottom margin 208. As the lowermost tip of the margin 208 comes into contact with the mat extension 212, therefore, liquid will be drawn from it through the restricted path it affords onto the absorbent mat material. When the amount of liquid removed has produced a sufficient displacement of the centre of gravity, the carriage tilts back to its illustrated position and the supply of liquid from the reservoir to the screen is resumed.

The apparatus is thus self-regulating in that liquid that has not evaporated while flowing down the screen, in particular lower volatility components, is drawn off if it has accumulated excessively, and at the same time the supply of further liquid is cut off to ensure that the liquid held on the screen quickly falls below the saturation point. Because the pivotal support 184, 186 is at the bottom of the carriage the centre of gravity is also displaced by each tilting movement in the direction of tilt to give a hysteresis effect which maintains the carriage stably in its new position. The gravity forces also act to press the spigots, and their associated wicks, firmly together when the flow path to the screen is established.

Any surplus liquid drawn from the screen is easily contained in the larger mass of the mat and can continue to diffuse into the atmosphere from there. Meanwhile the impediment to flow down the screen has been removed and the screen immediately receives fresh liquid from the reservoir. The more volatile components of the liquid to be dispersed are thus essentially continuously supplied to and dispersed from the screen when the carriage is in its illustrated position.

For convenience, the reservoir 166 is held detachably in the frame 164, being retained by a pair of vertically spaced spigots 222 which are inserted into sockets 224 on the frame. It has a body of transparent or translucent material through which the level of liquid is visible and is provided with a handle 226 and in its top face a small filler hole 228 that serves as a vent during the operation of the apparatus.

The dispersal of material from the dispenser can be increased by providing a forced flow of air, as already mentioned. Thus, a rotary fan (not shown) can be located above the mat and screens, with its axis vertical, so as to direct the air flow along their faces.

It will be understood that the self-regulating mechanism employing a movable carriage as described can be reconfigured so that the supporting pivot is located in the upper region of the apparatus and the carriage is suspended from it. In general, however, it will be preferred to locate the pivot support below the centre of gravity to limit the frequency of displacement of the screen, but it may be chosen to be at a higher or lower level to reduce or increase respectively the hysteresis effect of the movement of the centre of gravity.

In all the examples described above the dispersal screen acts as a slow release device for the limited amount of volatile material held by the screen at any instant. As it moves across the screen and diffuse into the atmosphere this material is continuously replaced from the reservoir where the liquid is held substantially sealed from the surrounding air so that its composition remains stable.

While there are advantages to be obtained by employing screens of the form described in the earlier examples with the regulated level liquid reservoirs described in the later examples, it should be understood that it is possible within the scope of the invention to provide a liquid dispenser with a regulated level liquid reservoir as described herein, using any form of dispersal screen or body to dispense the liquid supplied from the reservoir.

It will also be understood that many modifications can be made within the scope of the invention. In particular individual features of the preceding examples of apparatus according to the invention can be employed in embodiments other than those in which they have been specifically described, although to avoid prolixity the alternative combinations of features have not been explicitly set out. For example, a constant-level reservoir arrangement such as that shown in FIG. 6 can be employed in combination with a regulating screen arrangement such as that shown in FIGS. 17 and 18.

As another example of a modification within the scope of the invention the dispenser may be embodied in an apparatus comprising a ventilating fan and an air flow path in which the dispersal screen or screens of the dispenser is located. In one form, it may be arranged that there is a holder in which a disposable dispenser can be inserted, to put the screen of the dispenser in the path of the flow through the fan.

In addition, although many of the examples have been described with specific reference to the dispersal of volatile materials into the atmosphere, the invention can also be employed for the dispersal of materials into a surrounding liquid or into a flow of liquid.

What is claimed is:

1. A dispenser for a volatile material comprising a reservoir containing the material as a liquid, and a diffusing screen from which the material can evaporate or volatilise into the surrounding atmosphere, said screen being in flow communication with the liquid in the reservoir downwardly from an entry edge at which the liquid is transferred to the screen from the reservoir and comprising a fabric having at least a first series of generally parallel threads of a plurality of filaments, the threads of said first series being arranged in spaced groups in which the threads of a group are more closely spaced than in the spaces between the groups, said groups of threads being arranged to exercise a capillary action on the liquid reaching the screen from the reservoir.

2. A dispenser according to claim 1 wherein said first series of threads are interwoven with a second series of threads being arranged in spaced groups transverse thereto there being spaces between said spaced group of threads of said second series at least as great as said spaces between the groups of the first series of threads.

3. A dispenser according to claim 1 wherein absorbent means are provided at a lower boundary of the screen to take up liquid flowing down the screen to said boundary.

4. A dispenser according to claim 1 having a refillable supply container having an inlet valve communicating with the top of the container and an outlet valve communicating with the bottom of the container, said valves being interconnected so that opening one valve closes the other valve.

5. A dispenser according to claim 1 having at least one transfer member comprising a plurality of capillary passages to transfer the liquid from the reservoir to the screen.

6. A dispenser according to claim 5 wherein the transfer member is shielded from the surrounding atmosphere.

7. A dispenser according to claim 1 wherein the screen is held in a rigid surrounding frame.

8. A dispenser according to claim 1 wherein the screen is in the form of at least one pleated or folded sheet.

9. A dispenser according to claim 1 wherein the screen comprises a plurality of superimposed layers of fabric.

10. A dispenser according to claim 1 wherein a plurality of spaced screens are connected to the reservoir in parallel.

11. A dispenser according to claim 10 wherein the screens are detachably mounted to a common supply manifold from the reservoir.

12. A dispenser according to claim 1 further comprising means for directing a flow of air onto the screen.

13. A dispenser for a volatile liquid comprising a reservoir for the liquid and a fluid conduit providing a flow path extending upwardly from the reservoir to an upper region of a downwardly extending, laminar dispersal or diffusion screen, said fluid conduit having means for drawing liquid from the reservoir to said screen upper region to allow the liquid to flow by gravity down the screen as it is dispersed therefrom to the surrounding atmosphere.

14. A dispenser according to claim 13 wherein the screen is formed from a woven fabric having a first series of threads extending downwardly and having spaces between the individual threads or groups of the threads wider than the thickness of the threads.

15. A dispenser according to claim 13 or claim 14 further comprising a holding element for receiving surplus liquid from a lower region of the screen.

16. A dispenser according to claim 13 or claim 14 comprising means responsive to the amount of liquid on the screen for interrupting the flow of liquid to the screen from the reservoir whereby to limit the amount of material held on the screen.

17. A dispenser according to claim 16 wherein the screen is tiltably supported for pivoting movement to and fro to alternately interrupt and complete the fluid path from the reservoir to the screen.

18. A dispenser according to claim 17 wherein the screen is arranged to be tilted to interrupt said flow in dependence upon a shift of centre of gravity by the accumulation of surplus liquid on the screen.

19. A dispenser according to claim 16 comprising a holding element for receiving surplus liquid from the screen to accelerate the re-establishment of liquid flow from the reservoir to the screen.

20. A dispenser according to claim 15 wherein said holding element comprises a sheet or mat connected or connectable to said screen through a fluid path of restricted cross-section relative to said sheet or mat.

21. A dispenser according to claim 13 wherein the reservoir comprises a chamber supplied from above from a container having a bottom outlet, the reservoir being open to atmosphere above the level of said bottom outlet, the fluid conduit extending from a chamber outlet below said container outlet for leading liquid from the chamber to the screen, the arrangement being such that lowering of the liquid level in the chamber below said supply container bottom outlet by the removal of liquid through said conduit allows further liquid to flow from the container into the chamber to maintain the liquid level therein.

22. A dispenser according to claim 21 wherein a replaceable sealed supply container is provided to supply liquid to the reservoir and means are provided for opening the container to form said bottom outlet when locating it in the dispenser.

23. A dispenser according to claim 21 wherein the container is provided with a sealable filler port.

24. A dispenser according to claim 23 wherein valve means are provided for said filler port and to interrupt communication between the container and the reservoir simultaneously with the opening of the filler port.

25. A dispenser according to claim 13 wherein the screen comprises a fabric having at least a first series of generally parallel threads, the threads of said first series being arranged in spaced groups in which the threads of a group are more closely spaced than in the spaces between the groups, said groups of threads being arranged to exercise a capillary action on the liquid reaching the screen from the reservoir.

26. A dispenser according to claim 25 comprising means for maintaining a substantially constant liquid level in a space open to atmosphere in the supply path to the screen.

27. A dispenser for a volatile liquid comprising a reservoir for the liquid and a fluid conduit providing a flow path from the reservoir to an upper region of a downwardly extending, laminar dispersal or diffusion screen, said fluid conduit having means for drawing liquid from the reservoir to said screen upper region to allow the liquid to flow by gravity down the screen as it is dispersed therefrom, a secondary pad or mat for receiving surplus liquid from said downwardly extending screen being connected to a lower region of said screen through a flow path of limited cross-section.

\* \* \* \* \*